United States Patent [19]

Luebcke

[11] 4,241,833
[45] Dec. 30, 1980

[54] PARAMEDIC KIT

[76] Inventor: Dean E. Luebcke, 453 E. 101st Ave., Crown Point, Ind. 46307

[21] Appl. No.: 67,752

[22] Filed: Aug. 20, 1979

[51] Int. Cl.³ .................. B65D 6/02; B65D 25/02; B65D 43/16
[52] U.S. Cl. .................................... 206/570; 206/373; 190/51; 190/52; 312/283; 312/290
[58] Field of Search ............... 206/570, 373, 372, 349, 206/473, 480; 190/16, 51, 52; 312/DIG. 33, 283, 290

[56] References Cited

U.S. PATENT DOCUMENTS

| | | | |
|---|---|---|---|
| 328,588 | 10/1885 | Jordan | 190/52 |
| 1,113,832 | 10/1914 | Roth | 190/52 |
| 1,405,422 | 2/1922 | Kennedy | 206/373 |
| 1,657,854 | 1/1928 | Clemensen | 206/372 |
| 2,062,973 | 12/1936 | Gluckstein | 206/570 |
| 2,584,048 | 1/1952 | Ramsey | 190/51 |
| 2,895,600 | 7/1959 | Nevins | 312/DIG. 33 |

Primary Examiner—William T. Dixson, Jr.
Attorney, Agent, or Firm—Walter Leuca

[57] ABSTRACT

This invention is a paramedic airway kit. It comprises a case, interiorly divided into two compartments by a partition. A front wall serving as a door is hinged to the partition and pivotable to planularly extend the partition in the open position and thereby serve as an extended shelf. A second front wall, also serving as a door, is hinged to the base of the case and pivotable to planularly extend the base when in the open position and thereby expanding the perimeter of the base to render the case stable. The interior side of the first mentioned door is provided with anchor means for oropharyngeal airways. A plurality of article constraining straps are provided on the interior side of the first mentioned door to permanently locate articles used by a paramedic. On the interior side of the back wall of the case is provided a block member on which is mounted a mask for a bag mask resuscitator.

5 Claims, 5 Drawing Figures

PARAMEDIC KIT

BACKGROUND OF THE INVENTION

1. Field of the Invention

This invention relates generally to a paramedic kit and more particularly to an airway kit.

2. Description of the Prior Art

The prior art problem that this invention is directed to is the problem of providing quick and easy access to essential equipment required in administering life sustaining emergency treatment for cardiac arrest patients in emergency situations. Certain items necessary for such treatment were carried in bags or cases having no special provision for securing such items at a permanent location. Because these items were not thus secured in permanent locations, they were not readily found especially when working in adverse life threatening situations. Also, since these items were not secured in a permanent location in the prior art case, it was not noticed if some of the items were missing, if in fact they were.

SUMMARY OF THE INVENTION

Accordingly, I have invented a kit especially adapted for paramedic use particularly provided with anchor means to secure airway emergency items in permanent locations therein which are easily and rapidly accessible to the user and which case when opened forms an extendable base rendering the kit stable and secure in its open position.

Other objects and advantages of my invention will become more apparent after a careful study of the following detailed description taken together with the accompanying drawings which illustrate a preferred embodiment of my invention.

DESCRIPTION OF THE PREFERRED EMBODIMENT

Figure 1:
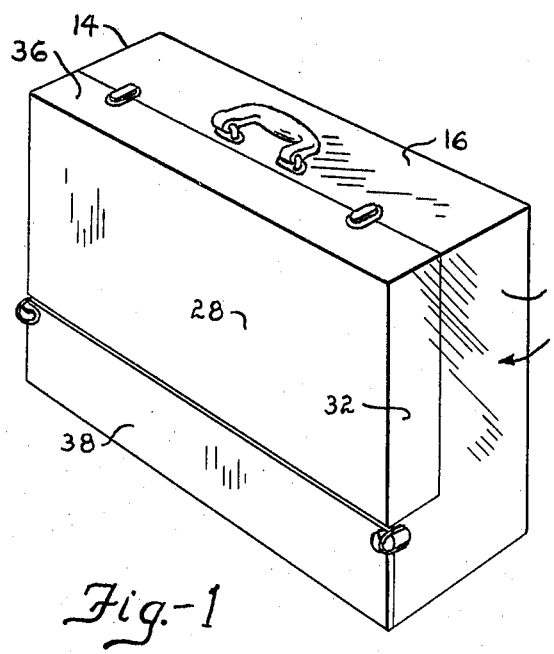
FIG. 1 is a perspective view of the airway kit of my invention shown in the closed position.
Figure 4:
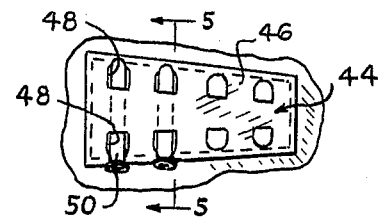
FIG. 4 is a plan view of an oropharyngeal airway anchor.
Figure 3:
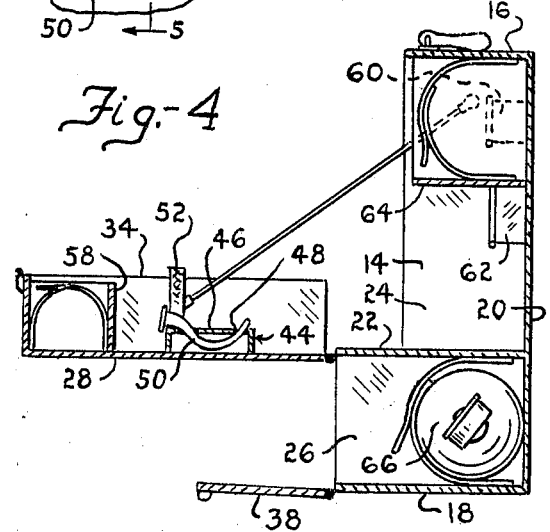
FIG. 3 is an end view section thereof taken along lines 3—3 of FIG. 2.
Figure 5:
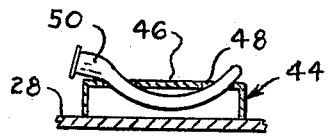
FIG. 5 is an end section of the oropharyngeal airway anchor taken along lines 5—5 of FIG. 4.
Figure 2:
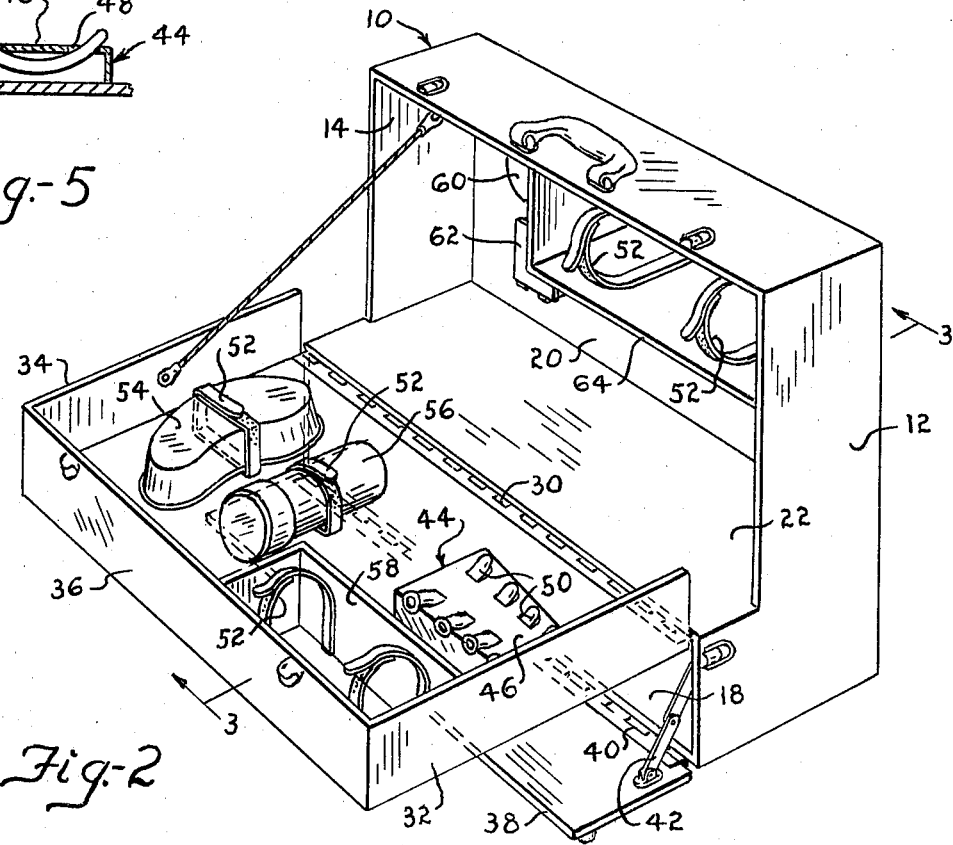
FIG. 2 is a perspective view of the airway kit of my invention shown in the open position.

Referring now to the drawings wherein is illustrated a preferred embodiment of my invention, numeral 10 designates generally the kit of my invention. It comprises opposing L-shaped end walls 12 and 14, top and bottom walls 16 and 18 and back wall 20. Interiorly, the kit is partitioned as at 22 to form upper and lower compartments 24 and 26. Compartment 24 is covered by front wall 28 which is hinged to partition 22 by hinge strip 30. Front wall 28 carries opposing end walls 32 and 34 and top wall 36 which are planularly aligned with end walls 12 and 14, respectively, and top wall 16 of kit 10 when front wall 28 is pivoted upwardly to close compartment 24. The bottom compartment 26 is pivoted with front wall 38 which is hingedly connected to the bottom wall 18 by means of hinge strap 40 so as to close the bottom compartment when the bottom front wall is pivoted upwardly. When the bottom wall 38 is pivoted downwardly to open the second compartment and locked in place by elbow link 42, it forms a planular extension of bottom wall 18 thereby expanding the base of kit 10 and thereby render the kit stable when front wall 28 is open.

I provide anchor means 44 on the interior side of front wall 28 to contain oropharyngeal airways 50 which are flat, plastic tubes which are inserted through the mouth of an unconscious patient to keep an airway open.

Anchor means 44 is preferably a rigid plastic sheet 46 supported around the perimeter thereof, elevated from wall 28 on the interior side and formed with a series of hole pairs 48, each of the hole pairs 48 being spaced to accommodate different length tubes 50 through which hole pairs 48 said tubes may be inserted and therein fixed. Also provided on the interior side of front wall 28 are a plurality of fastening straps 52 such as Velcro tapes anchored to the wall at spaced locations which secure in a permanent place other items such as an emesis basin 54 and a suction unit 56. I further provide an open compartment 58 for containing nasopharyngeal airway tubes (not illustrated). Also provided on the interior side of back wall 20 is mount block 60 for securing thereto a mask from a bag mask resuscitator, and if desired a cover case 62 for containing capsules of ammonia inhalant. Open compartment 64 is provided to contain in place endotracheal tubes and intubation equipment. The lower compartment 26 contains oxygen tank unit 66.

In the operation of this invention, the paramedic secures in a permanent location within kit 10 of this invention the oropharyngeal airway and other items such as emesis basin, suction unit, nasopharyngeal airway tubes, bag mask resuscitator, oxygen mask and cannula, ammonia inhalant, endotracheal tubes and intubation equipment and the oxygen tank unit, so that any of these items may be easily and readily retrieved from the kit particularly when working in life threatening situations. Also a visual inspection will quickly reveal if any of the necessary life sustaining items are missing prior to departing in response to an emergency call.

Further, bottom compartment door 38 serves as an extended base rendering kit 10 stable in its upright position when top compartment door 28 is opened for an orderly and rapid handling of the life sustaining units contained therein. Kit 10 is rendered stable by dimensioning the width of bottom door 38 so that the center of gravity of the kit, when the top door 28 is in the open position, does not extend beyond the edge of the bottom door when planularly aligned with base 18.

I claim:

1. An airway kit, comprising:
    end walls, base and top walls and a back wall;
    a partition wall extending between said end walls and parallel to said base and top walls;
    a front wall hinged to said partition wall pivotable to planularly extend said partition when in the open position, and to abut against said end and top walls when in the closed position;
    a second front wall hinged to said base wall pivotable to planularly extend said base wall when in the open position, and to abut against said end and partition walls when in the closed position;
    anchor means fixed to the interior side of said top front wall, said anchor means being a sheet member supported around the perimeter thereof and having a plurality of hole pairs;

oropharyngeal airways fitted in said hole pairs of said anchor means;

a plurality of straps fixed to the interior side of said front wall, the ends of each of said straps connecting together to form constraining means;

a block member on the interior side of said back wall; and a mask from a bag mask resuscitator mounted on said block member.

2. The paramedic airway kit of claim 1 wherein the second front wall when positioned to planularly extend said base is further characterized as extending beyond the center of gravity of said kit when said first front wall is opened to planularly extend said partition wall.

3. The paramedic kit of claim 1 wherein each of said hole pairs in said sheet member is further characterized as being spaced apart different distances to accommodate different length oropharyngeal airways.

4. A case for a paramedic kit comprising:

end walls, base and top walls and a back wall;

a partition wall extended between said end walls and parallel to said base and top walls;

a front wall hinged to said partition wall pivotable to planularly extend said partition when in the open position, and to abut against said end and top walls when in the closed position; and a second front wall hingedly connected to said base wall pivotable to planularly extend said base wall when in the open position, and to abut against end and partition walls when in the closed position.

5. The case of claim 4 wherein said partition wall is further characterized as being spaced from said top wall and said base wall to provide a major compartment between said partition and top walls, and a minor compartment between said partition and base walls.

* * * * *